United States Patent [19]

Zink et al.

[11] Patent Number: 4,766,211
[45] Date of Patent: Aug. 23, 1988

[54] CHROMOGENIC QUINAZOLINES

[75] Inventors: Rudolf Zink, Therwil; Ian J. Fletcher, Magden, both of Switzerland

[73] Assignee: Ciba-Geigy Corporation, Ardsley, N.Y.

[21] Appl. No.: 901,090

[22] Filed: Aug. 27, 1986

[30] Foreign Application Priority Data

Sep. 6, 1985 [CH] Switzerland .................. 3855/85

[51] Int. Cl.$^4$ .................................. C07D 237/26
[52] U.S. Cl. ..................... 544/58.6; 544/62; 544/74; 544/79; 544/105; 544/116; 544/119; 544/284; 544/287; 544/289
[58] Field of Search ............ 544/58.6, 62, 74, 79, 544/105, 116, 119, 284, 287, 289

[56] References Cited

U.S. PATENT DOCUMENTS

| | | | |
|---|---|---|---|
| 4,435,003 | 3/1984 | Fletcher | 282/27.5 |
| 4,480,096 | 10/1984 | Fletcher | 544/289 |
| 4,555,569 | 11/1985 | Zink et al. | 544/105 |
| 4,625,027 | 11/1986 | Zink et al. | 544/284 X |
| 4,668,966 | 5/1987 | Zink et al. | 544/284 X |

FOREIGN PATENT DOCUMENTS 172379 10/1983 Japan.

OTHER PUBLICATIONS

Manhas et al., Chemical Abstracts, vol. 91 (1979), 157681z.

Primary Examiner—Richard L. Raymond
Attorney, Agent, or Firm—Edward McC. Roberts; Meredith C. Findlay

[57] ABSTRACT

Chromogenic quinazolines of formula

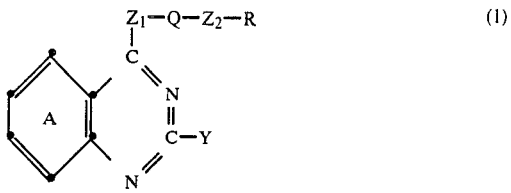

wherein
R is an aryl radical or a heterocyclic radical,
$Z_1$ is oxygen or sulfur,
$Z_2$ is oxygen, sulfur or $$-\underset{|}{N}R',$$

R' is hydrogen, alkyl which is unsubstituted or substituted by halogen, cyano or lower alkoxy, or is cycloalkyl, phenyl, benzyl, phenethyl or acyl, or —NRR' is a 5- or 6-membered heterocyclic radical,
Q is an aliphatic radical which may be interrupted by a further member $Z_2$,
Y is the radical of a couplable compound, and the ring
A is unsubstituted or substituted by halogen, cyano, nitro, lower alkyl, lower alkoxy or lower alkoxycarbonyl.

These quinazolines are exceedingly fast to sublimation and are particularly suitable color formers in pressure-sensitive or heat-sensitive recording materials and give strong and lightfast yellow and orange colorations.

16 Claims, No Drawings

CHROMOGENIC QUINAZOLINES

The present invention relates to chromogenic quinazolines, to their preparation, and to the use thereof as colour formers in pressure-sensitive and heat-sensitive recording materials.

The quinazolines of this invention conform to the general formula

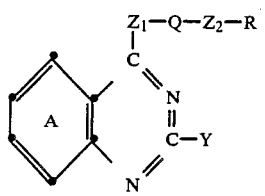  (1)

wherein
R is an aryl radical or a heterocyclic radical,
$Z_1$ is oxygen or sulfur,
$Z_2$ is oxygen, sulfur or

R' is hydrogen, alkyl of not more than 12 carbon atoms, unsubstituted or substituted by halogen, cyano or lower alkoxy, or is $C_5$-$C_6$cycloalkyl, phenyl, benzyl, phenethyl or $C_1$-$C_{12}$acyl, or —NRR' is a 5- or 6-membered, preferably saturated, heterocyclic radical,
Q is an aliphatic radical which may be interrupted by a further member $Z_2$,
Y is the radical of a couplable compound, and the ring
A is unsubstituted or substituted by halogen, cyano, phenyl, nitro, lower alkyl, lower alkoxy, $C_1$-$C_4$acylamino, or lower alkoxycarbonyl.

In the definition of the radicals of the quinazolines, lower alkyl and lower alkoxy normally denote those groups or moieties that contain 1 to 5, preferably 1 to 3, carbon atoms. Examples of lower alkyl groups are methyl, ethyl, n-propyl, isopropyl, n-butyl, sec-butyl, tert-butyl, amyl or isoamyl; and lower alkoxy groups are for example methoxy, ethoxy, isopropoxy, tert-butoxy or tert-amyloxy.

Acyl is preferably formyl, lower alkylcarbonyl such as acetyl or propionyl, or benzoyl. Further acyl radicals are lower alkylsulfonyl, e.g. methylsulfonyl or ethylsulfonyl and phenylsulfonyl.

Halogen in formula (1) and in the subsequent formulae is e.g. fluorine, bromine or, preferably, chlorine.

R is preferably an aryl radical.

An aryl radical R is e.g. phenyl, biphenylyl or naphthyl. These aryl radicals may be substituted by halogen, cyano, nitro, lower alkyl, lower alkoxy, lower alkoxycarbonyl or lower alkylcarbonyl. An aryl radical R is preferably phenyl, chlorophenyl, methoxyphenyl, tolyl or xylyl.

A heterocyclic radical R is preferably a 5- or 6-membered heterocycle of aromatic character which preferably contains oxygen, sulfur or nitrogen. Examples of such heterocycles are thienyl, furyl, pyrrolyl, pyrazolyl, imidazolyl or, preferably, pyridyl. These heterocyclic radicals may be substituted, preferably by halogen, cyano, lower alkyl, lower alkoxy or lower alkoxycarbonyl, and/or may contain fused benzene rings.

The heterocyclic radical R may also be saturated and is for example pyrrolidino, piperidino, pipecolino, morpholino, thiomorpholino, piperazino, or N-methylpiperazino. Preferred saturated hetercyclic radicals R are pyrrolidino, piperidino or morpholino. Q is preferably an alkylene group which may contain from 2 to 8 carbon atoms and may be straight chain or branched. The alkylene group preferably contains 2 to 4 carbons and is e.g. a member selected from —$CH_2$—$CH_2$—$CH_2$—,

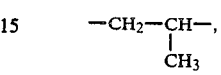

—$CH_2$—$CH_2$—$CH_2$—$CH_2$—,

and preferably —$CH_2$—$CH_2$—.

The aliphatic hydrocarbon radical may be interrupted by oxygen atoms, sulfur atoms or imino groups —NR'—, in which case Q is preferably a radical of formula

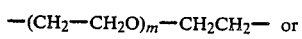

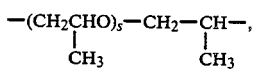

wherein m is 1 to 4, preferably 1 or 2, and s is 1 or 2. The preferred meaning of Q is —$CH_2CH_2$—.

If $Z_2$ is —NR' and —NRR' is a 5- or 6-membered heterocycle, said heterocycle is for example pyrrolidino, piperidino, pipecolino, piperazino or, preferably, morpholino.

Each of $Z_1$ and $Z_2$ is preferably oxygen.

Suitable couplable compounds represented by Y are preferably aromatic amines such as N-monosubstituted or N,N-disubstituted anilines or naphthylamines, aromatic cyclic imides such as N-unsubstituted or N-substituted indoles, carbazoles, oxazines or thiazines, or polynuclear non-aromatic heterocyclic compounds such as N-unsubstituted or N-substituted indolines, tetrahydrocarbazoles, dihydroquinolines or tetrahydroquinolines, dibenzylimides or benzomorpholines. Further, Y is attached to the quinoline moiety through the fused benzene ring of the said heterocycles. Preferred non-aromatic heterocyclic compounds are indolines, tetrahydroquinolines and benzomorpholines.

Especially preferred for the introduction of Y are N,N-disubstituted anilines or C-substituted and/or N-substituted tetrahydroquinolines.

The mononuclear or polynuclear carbocyclic or heterocyclic couplable compounds may also carry one or more ring substituents. Examples of possible C-substituents are: halogen, hydroxyl, cyano, nitro, lower alkyl, lower alkoxy, lower alkoxycarbonyl, $C_1$-$C_8$acyl, preferably lower alkylcarbonyl, $C_3$-$C_6$alkylene, $C_5$-$C_6$cycloalkyl, benzyl or phenyl. Examples of N-substituents are: $C_1$-$C_{12}$alkyl, $C_2$-$C_{12}$alkenyl, benzyl or phenylethyl, each of which may also be substituted e.g. by cyano, halogen, nitro, hydroxyl, lower alkyl, lower alkoxy or lower alkoxycarbonyl.

The alkyl and alkenyl radicals may be straight chain or branched. Alkyl radicals are e.g. methyl, ethyl, n-propyl, isopropyl, n-butyl, tert-butyl, sec-butyl, amyl, n-hexyl, 2-ethyl-n-hexyl, isooctyl, n-octyl, decyl or n-dodecyl. Examples of alkenyl groups are vinyl, allyl, 2-methylallyl, 2-ethylallyl, 2-butenyl or octenyl.

The ring A is preferably not furhter substituted. If it does contain substituents, then it is preferably substituted by one or two members selected from halogen, cyano, phenyl, lower alkyl and lower alkoxy, e.g. by cyano, chloro, methyl or methoxy.

Useful chromogenic quinazolines are those of formula

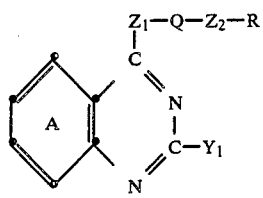

(2)

wherein A, $Z_1$, $Z_2$, Q and R have the given meanings and $Y_1$ is an aminophenyl radical of formula

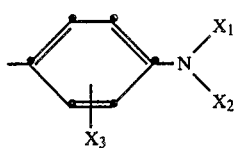

(2a)

or a hydrogenated heterocyclic radical of formula

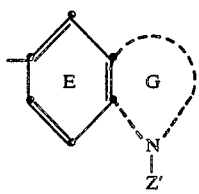

(2b)

wherein
$X_1$ and $X_2$ are each independently of the other hydrogen, alkyl of not more than 12 carbon atoms, unsubstituted or substituted by halogen, hydroxy, cyano or lower alkoxy, or are $C_5$–$C_6$cycloalkyl, phenyl, benzyl, phenethyl, or phenyl or benzyl, each substituted by halogen, nitro, cyano, lower alkyl, lower alkoxy or lower alkoxycarbonyl, or $X_1$ and $X_2$, together with the nitrogen atom to which they are attached, are a 5- or 6-membered, preferably saturated, heterocyclic radical, and $X_3$ is hydrogen, halogen, nitro, lower alkyl, lower alkoxy or lower alkoxycarbonyl, and Z' is hydrogen or alkyl of not more than 8 carbon atoms, unsubstituted or substituted by halogen, cyano or lower alkoxy, or is $C_5$–$C_6$cycloalkyl, benzyl or phenethyl, and the ring E is unsubstituted or substituted by cyano, halogen, lower alkyl, e.g. methyl, or lower alkoxy, e.g. methoxy, and the ring G is a hydrogenated 5- or 6-membered N-heterocycle which may contain a further hetero atom, e.g. oxygen, sulfur or nitrogen, as ring member, and is unsubstituted or C-substituted by one or (depending on the substituents) more members selected from halogen, cyano, hydroxyl, lower alkyl, lower alkoxy, $C_1$–$C_4$acylamino, $C_5$–$C_6$cycloalkyl, benzyl and $C_3$–$C_6$alkylene.

$X_1$ and $X_2$ as alkyl groups may be straight chain or branched. Examples of such alkyl radicals are methyl, ethyl, n-propyl, isopropyl, n-butyl, sec-butyl, amyl, n-hexyl, 2-ethyl-n-hexyl, n-octyl, isooctyl or n-dodecyl.

$X_1$ and $X_2$ as substituted alkyl groups are preferably cyanoalkyl, haloalkyl, hydroxyalkyl or alkoxyalkyl containing preferably a total of 2 to 4 carbon atoms, e.g. β-cyanoalkyl, β-chloroethyl, β-hydroxyethyl, β-methoxyethyl or β-ethoxyethyl.

$X_1$ and $X_2$ as cycloalkyl are e.g. preferably cyclohexyl. The cycloalkyl radicals may contain one or more $C_1$–$C_4$alkyl moieties, preferably methyl groups. Preferably they contain a total of 5 to 10 carbon atoms.

Preferred substituents of the benzyl and phenyl moiety of $X_1$ and $X_2$ are e.g. halogen, cyano, methyl, methoxy or carbomethoxy. Examples of such araliphatic and aromatic radicals are methylbenzyl, chlorobenzyl, cyanophenyl, tolyl, xylyl, chlorophenyl, methoxyphenyl or carbomethoxyphenyl.

A heterocyclic radical —$NX_1X_2$ is e.g. pyrrolidino, piperidino, pipecolino, morpholino, thiomorpholino or piperazino such as N-methylpiperazino. Preferred heterocyclic radicals —$NX_1X_2$ are pyrrolidino, piperidino or morpholino.

$X_1$ and $X_2$ are each independently of the other preferably lower alkyl, benzyl, phenyl, phenethyl, lower alkylphenyl or lower alkoxyphenyl. $X_3$ is preferably hydrogen, chlorine, methyl, methoxy or ethoxy.

The ring E is preferably unsubstituted, but it can with advantage contain a methyl group. The ring G is preferably 6-membered and C-substituted preferably by 1, 2 or 3 methyl groups.

Z' is preferably lower alkyl, benzyl or β-cyanoethyl.

Preferred quinazolines of formula (2) are those in which $Y_1$ is a radical of formula (2a).

Interesting chromogenic quinazolines are those of formula

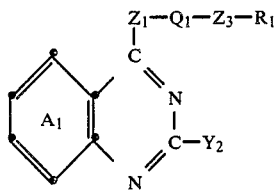

(3)

wherein
$R_1$ is a phenyl or naphthyl radical, each unsubstituted or substituted by halogen, methyl or methoxy,
$Z_1$ is oxygen or sulfur,
$Z_3$ is oxygen, sulfur, —NH— or —NR", R" is lower alkyl or —$NR_1R''$ is morpholino,
$Q_1$ is $C_2$–$C_4$alkylene or the radical —(CH$_2$—CH$_2$—O)$_{m1}$—CH$_2$CH$_2$—,
$Y_2$ is an aminophenyl radical of formula

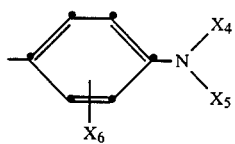

or a 5-indolinyl radical of formula

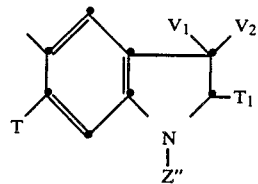

a tetrahydroquinolinyl radical of formula

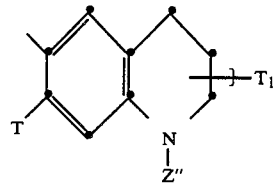

a tetrahydroquinolinyl radical of formula

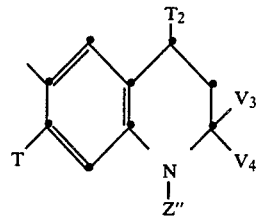

or a benzomorpholino radical of formula

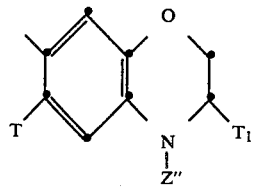

wherein $m_1$ is 1 to 3, $X_4$ and $X_5$ are each independently of the other lower alkyl, cyanolower alkyl, benzyl, phenyl, phenethyl, lower alkylphenyl or lower alkoxyphenyl; or $X_4$ and $X_5$, together with the nitrogen atom to which they are attached, are pyrrolidino, piperidino or morpholino, $X_6$ is hydrogen, halogen, lower alkyl or lower alkoxy, $Z''$ is hydrogen, $C_1$-$C_8$alkyl, $C_2$-$C_6$alkoxyalkyl, β-cyanoethyl, benzyl or phenethyl, T is hydrogen, halogen, lower alkyl, lower alkoxy, $C_1$-$C_4$acylamino, for example acetylamino or propionylamino, or is phenyl, $T_1$ and $T_2$ are each hydrogen, halogen, hydroxy, lower alkyl or lower alkoxy, and $V_1$, $V_2$, $V_3$ and $V_4$ are each hydrogen, lower alkyl, $C_5$-$C_6$cycloalkyl or benzyl; or ($V_1$ and $V_2$) or ($V_3$ and $V_4$) are each together $C_4$-$C_5$alkylene, and and the ring $A_1$ is unsubstituted or substituted by one or two members selected from cyano, halogen, lower alkyl, phenyl and lower alkoxy.

Among the quinazolines of formula (3), those compounds are preferred in which $Y_2$ is an aminophenyl radical of the formula (3a). $X_4$ and $X_5$ are lower alkyl or benzyl. $X_6$ is preferably hydrogen. $R_1$ is preferably phenyl or chlorophenyl. $Q_1$ is preferably ethylene or propylene. $Q_1$ is preferably also —CH$_2$CH$_2$—O—CH$_2$CH$_2$—. $Z_1$ and $Z_3$ are preferably oxygen. The ring $A_1$ is preferably unsubstituted.

In the quinazolines of the formula (3), wherein $Y_2$ is a radical of formula (3b), (3c), (3d) or (3e), the N-substituent $Z''$ is preferably benzyl, β-cyanoethyl, or $C_1$-$C_8$alkyl, e.g. n-octyl, n-butyl, isopropyl or, most preferably, methyl or ethyl.

$Y_2$ is preferably the tetrahydroquinolinyl radical of formula (3d) or primarily the benzomorpholino radical of formual (3e). T is preferably hydrogen or methyl. $T_1$ is preferably hydrogen, methyl, hydroxyl or chlorine. $T_2$ is preferably hydrogen, methyl or ethyl. $V_1$ and $V_2$ are preferably hydrogen or methyl; and $V_3$ and $V_4$ are each preferably lower alkyl and, most preferably, are each methyl.

If ($V_1$ and $V_2$) or ($V_3$ and $V_4$) together are alkylene, then they contain preferably 4 or 5 carbon atoms and, together with the carbon atom to which they are attached, form a cyclopentane or cyclohexane ring.

Particularly interesting quinazolines are those of formula

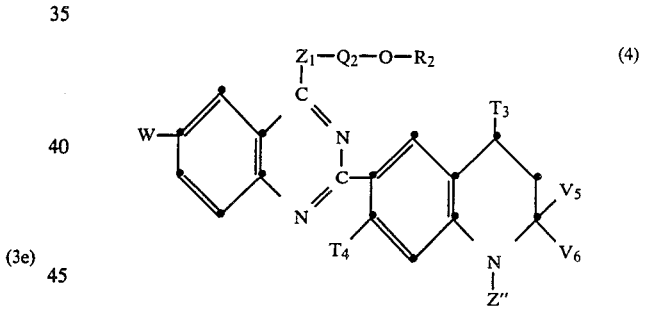

or, most particularly, those of formula

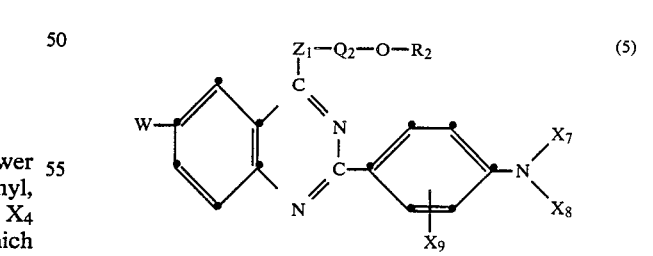

wherein $Q_2$ is straight chain or branched $C_2$-$C_4$alkylene, $R_2$ is phenyl, chlorophenyl, tolyl, methoxyphenyl or naphthyl, $Z_1$ is sulfur or, preferably, oxygen, $X_7$ and $X_8$ are each lower alkyl or benzyl; or —$NX_7X_8$ is piperidino, $X_9$ is hydrogen, methyl, methoxy or ethoxy, $Z''$ is $C_1$-$C_8$alkyl, β-cyanoethyl or benzyl, T₃, V₅ and V₆ are each lower alkyl, preferably methyl or ethyl, T₄ is hydrogen or methyl, and W is halogen, methyl, methoxy or, preferably, hydrogen.

Preferred quinazoline compounds are those of formula (5), wherein $Q_2$ is preferably propylene or, most preferably, ethylene, or also —CH₂CH₂—O—CH₂CH₂—. $R_2$ is preferably phenyl or chlorophenyl. $X_7$ and $X_8$ are preferably benzyl or, most preferably, lower alkyl. W and $X_9$ are preferably hydrogen.

The quinazolines of formula (1) are prepared by reacting an alcohol or thioalcohol of formula

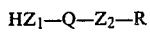    (6)

wherein R, Q, $Z_1$ and $Z_2$ have the given meanings, with a 4-haloquinazoline of formula

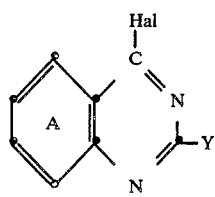    (7)

wherein A and Y have the given meanings and Hal is halogen, for example bromine, fluorine or, preferably, chlorine.

The reaction of the compound of formula (6) with the compound of formula (7) is conveniently carried out in the presence of an acid acceptor, e.g. an alkali metal hydroxide, alkali metal carbonate or a tertiary nitrogen base, e.g. pyridine or a trialkylamine, and preferably also in the presence of a quaternary ammonium salt, e.g. tetrabutylammonium bromide, optionally in an organic solvent or in an aqueous-organic two-phase medium, and in the temperature range from 60° C. to reflux temperature.

Suitable solvents are for example cycloaliphatic or aromatic hydrocarbons such as cyclohexane, benzene, toluene or xylene; chlorinated hydrocarbons such as chloroform, ethylene chloride or a chlorobenzene, preferably dichlorobenzene; ethers such as diethyl ether or glycol dimethyl ether; cyclic ethers such as dioxan or tetrahydrofuran; and dimethylformamide, diethylformamide, dimethylsulfoxide or acetonitrile.

Alcohols of formula (6) which may be employed as starting materials for the reaction with the quinazolines of formula (7) are preferably those of formula

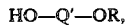    (8)

wherein Q' is C₂–C₈alkylene, or those of formula

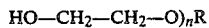    (9)

wherein n is 1 to 4 and is preferably 1 or 2.

Representative examples of alcohols employed as starting materials of formula (6) are: phenoxyethanol, chlorophenoxyethanol, phenoxypropanol, N-β-hydroxyethyl-N-ethylaniline, phenoxythioethanol, naphthyloxyethanol, phenoxydiglycol, phenoxydithioglycol, thioethanolaniline, N-(β-hydroxyethyl)morpholine.

The starting materials of formula (7) can be prepared by reacting e.g. a 2-aminobenzamide of formula

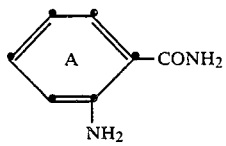    (10)

with an aldehyde of formula

    (11)

to give a 1,2,3,4-tetrahydroquinazol-4-one of formula

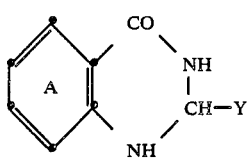    (12)

oxidising this compound to a compound of the formula

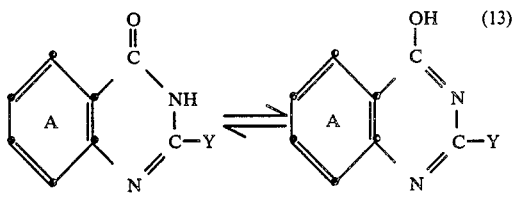    (13)

then replacing the hydroxyl group at the heterocyclic ring of the quinazoline system by a halogen atom, e.g. with phosphoroxy chloride in dichlorobenzene or with thionyl chloride in dimethylformamide, to give the starting material of formula (7). The 4-haloquinazoline can be further used without being isolated.

The oxidation of the reaction products of formula (12) to the 4-quinazolones of formula (13) is carried out with oxidising agents. Suitable oxidising agents are e.g. chromates, bichromates, chlorates, chlorites, peroxides, e.g. hydrogen peroxide, manganese dioxide, lead dioxide, molecular oxygen, air, perborates, permanganates, nitrites, chlorine, bromine and, in particular, chloranil or bisulfites.

The best results with respect to yield and purity of the 4-quinazolones are obtained with chloranil as preferred oxidising agent. The oxidation with sodium bisulfite affords ecological advantages. Following the procedure described in Synthesis 1981, (1), 35, quinazolones of formula (13) are obtained in good yield and purity using this oxidising agent.

4-Haloquinazolines of formula (7) and 4-quinazolones of formula (13), and the preparation thereof, are described for example in published European patent application No. 33716.

The quinazolines of formulae (1) to (5) are normally colourless or, at most, faintly coloured. When these sublimation-fast colour formers are brought into contact preferably with an acid developer, e.g. an electron acceptor, they produce strong yellow or orange shades of excellent light fastness. They are therefore also very useful when combined with one or more other known colour formers, for example 3,3-(bisaminophenyl)phthalides, 3,3-(bisindolyl)phthalides, 3-indolyl-3-aminophenylazaphthalides, 3-aminofluoranes, 2,6- diaminofluoranes, leucoauramines, spiropyranes, spirodipyranes, phenoxazines, phenothiazines, carbazolylmethanes or other triarylmethaneleuco dyes, to give blue, navy-blue, grey or black colorations.

The quinazolines of formulae (1) to (5) exhibit on phenolic substrates, and especially on activated clays and substituted zinc salicylates, an excellent colour intensity and lightfastness. They are particularly suitable as very rapidly developing colour formers for use in a heat-sensitive, or especially in a pressure-sensitive, recording material which can also be a copying material. They are distinguished by the property of having excellent solubility in the capsule oils and further of exhibiting a slight decrease in colour strength (CB decline) after exposure on a CB sheet. Compared with the closest quinazolines of the prior art, they have appreciably better fastness to sublimation.

A pressure-sensitive material consists, for example, of at least one pair of sheets which contain at least one colour former of formulae (1) to (5), dissolved in an organic solvent, and a solid electron acceptor as developer.

Typical examples of such developers are activated clays such as attapulgite, acid clay, bentonite, montmorillonite, activated clay, e.g. acid-activated bentonite or montmorillonite, and also zeolith, halloysite, silica, alumina, aluminium sulfate, aluminium phosphate, zinc chloride, zinc nitrate, activated kaolin or any clay, or acidic organic compounds, for example unsubstituted or ring-substituted phenols, salicylic acid or salicylates and their metal salts, or an acidic polymer, for example a phenolic polymer, an alkylphenol acetylene resin, a maleic acid/rosin resin or a partially or completely hydrolysed polymer of maleic acid and styrene, ethylene or vinyl methyl ether, or carboxypolymethylene. Mixtures of these polymers can also be used. Preferred developers are acid-activated bentonite, zinc salicylates, or the condensates of p-substituted phenols with formaldehyde. These last mentioned compounds may also contain zinc.

The developers may also be used in admixture with other basically inert or substantially inert pigments or with other auxiliaries such as silica gel or UV absorbers, e.g. 2-(2-hydroxyphenyl)benzotriazoles. Examples of such pigments are: talcum, titanium dioxide, zinc oxide, chalk, clays such as kaolin, as well as organic pigments, e.g. urea/formaldehyde condensates (BET surface area: 2-75 m$^2$/g) or melamine/formaldehyde condensates.

The colour former effects a coloured mark at those points where it comes into contact with the electron acceptor. To prevent the colour formers contained in the pressure-sensitive recording material from becoming active prematurely, they are usually separated from the electron acceptor. This separation can conveniently be accomplished by incorporating the colour formers in foam-like, sponge-like or honeycomb-like structures. The colour formers are preferably encapsulated in microcapsules, which can normally be ruptured by pressure.

When the capsules are ruptured by pressure, for example with a pencil, the colour former solution is transferred to an adjacent sheet which is coated with an electron acceptor and a coloured area is thus produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example a polyhalogenated paraffin such as chloroparaffin, or a polyhalogenated diphenyl such as monochlorodiphenyl or trichlorodiphenyl, and also tricresyl phosphate, di-n-butyl phthalate, dioctyl phthalate, trichlorobenzene, trichloroethylphosphate, an aromatic ether such as benzylphenyl ether, a hydrocarbon oil such as paraffin or kerosene, an alkylated (e.g. containing isopropyl, isobutyl, sec- or tert-butyl groups) derivative of diphenyl, diphenylalkane, naphthalene or terphenyl; dibenzyl toluene, terphenyl, partially hydrogenated terphenyl, a benzylated xylene, or other chlorinated or hydrogenated condensed aromatic hydrocarbons. Mixtures of different solvents, especially mixtures of paraffin oils or kerosene and diisopropylnaphthalene or partially hydrogenated terphenyl, are often used to obtain maximum solubility for the colour formation, a rapid and intense coloration, and a viscosity which is advantageous for the microencapsulation.

The capsules walls can be formed evenly around the droplets of the colour former solution by coacervation; and the encapsulating material may consist of gelatin and gum arabic, as described e.g. in U.S. Pat. No. 2,800,457. The capsules can also be formed conveniently from an aminoplast or a modified aminoplast by polycondensation, as described in British patent specification Nos. 989 264, 1 156 725, 1 301 052 and 1 355 124. Also suitable are microcapsules which are formed by interfacial polymerisation, e.g. capsules formed from polyester, polycarbonate, polysulfonamide, polysulfonate, but in particular from polyamide or polyurethane.

The microcapsules containing the colour formers of formulae (1) to (5) can be used for the production of a wide variety of known kinds of pressure-sensitive copying material. The various systems differ substantially from one another in the arrangement of the capsules, of the colour reactants, and of the support. A preferred arrangement is that in which the encapsulated colour former is in the form of a layer on the back of a transfer sheet and the developer is in the form of a layer on the face of a receiver sheet.

Another arrangement of the components is that wherein the microcapsules which contain the colour former, and the developer, are in or on the same sheet, in the form of one or more individual layers, or are present in the paper pulp.

The capsules are preferably secured to the support by means of a suitable adhesive. As paper is the preferred support, these adhesives are principally paper-coating agents, for example gum arabic, polyvinyl alcohol, hydroxymethylcellulose, casein, methyl cellulose, dextrin, starch or starch derivatives or polymer latices. These latter are e.g. butadiene/styrene copolymers or acrylic homopolymers or copolymers.

The paper employed comprises not only normal paper made from cellulose fibres, but also paper in which the cellulose fibres are replaced (partially or completely) by synthetic polymers.

The compounds of formulae (1) to (5) can also be employed as colour formers in a thermoreactive recording material. This recording material usually contains at least one carrier, one colour former, one electron acceptor, and optionally also a binder and/or wax.

Thermoreactive recording systems comprise, for example, heat-sensitive recording or copying materials or papers. These systems are used e.g. for recording information, for example in electronic computers, teleprinters or telewriters, or in recording and measuring instruments, e.g. electrocardiographs. The image (mark) formation can also be effected manually with a heated pen. Laser beams can also be used to produce heat-induced marks.

The thermoreactive recording material can be composed such that the colour former is dispersed or dissolved in one binder layer and the developer is dissolved or dispersed in the binder in a second layer. Another possibility comprises dispersing both the colour former and the developer in one layer. By means of heat the binder is softened at specific areas and the colour former comes into contact with the developer (electron acceptor) at those points where heat is applied and the desired colour develops at once.

Suitable developers are the same electron acceptors as are used in pressure-sensitive papers. Examples of developers are the clays already mentioned and especially phenolic resins, or also the phenolic compounds described e.g. in German Offenlegungsschrift No. 1 251 348, for example 4-tert-butylphenol, 4-phenylphenol, methylene bis(2-phenylphenol), 4-hydroxydiphenyl ether, α-naphthol, β-naphthol, 4-hydroxydiphenylsulfone, 4-hydroxy-4'-methyldiphenylsulfone, methyl 4-hydroxybenzoate, 4-hydroxyacetophenone, 2,2'-dihydroxydiphenyl, 4,4'-isopropylidenediphenol, 4,4'-isopropylidene-bis(2-methylphenol), 4,4'-bis(hydroxyphenyl)valeric acid, hydroquinone, pyrogallol, phloroglucinol, p-, m- and o-hydroxybenzoic acid, gallic acid, 1-hydroxy-2-naphthoic acid, as well as boric acid or organic, preferably aliphatic, dicarboxylic acids, for example tartaric acid, oxalic acid, maleic acid, citric acid, citraconic acid or succinic acid.

It is preferred to use fusible, film-forming binders for making the thermoreactive recording material. These binders are normally water-soluble, whereas the quinazolines and the developer are sparingly soluble or insoluble in water. The binder should be able to disperse and fix the colour former and the developer at room temperature.

When heated, the binder softens or melts, so that the colour former comes in contact with the developer and a colour is able to form. Examples of binders which are soluble, or at least swellable, in water are e.g. hydrophilic polymers, for example polyvinyl alcohol, polyacrylic acid, hydroxyethylcellulose, methyl cellulose, carboxymethylcellulose, polyacrylamide, polyvinyl pyrrolidone, butadiene/styrene copolymers, carboxylated butadiene/styrene copolymers, gelatin, starch, or etherified corn starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylacrylates, ethyl cellulose, nitrocellulose or polyvinyl carbazole. The preferred arrangement, however, is that in which the colour former and the developer are contained in one layer in a water-soluble binder.

The thermoreactive coatings may contain further auxiliaries. To improve the degree of whiteness, to facilitate the printing of papers, and to prevent the heated pen from sticking, the coatings may contain e.g. talcum, titanium dioxide, zinc oxide, aluminium hydroxide, calcium carbonate (e.g. chalk), clays or also organic pigments, for example urea/formaldehyde polymers. To effect the colour formation only within a limited temperature range, it is possible to add substances such as urea, thiourea, diphenyl thiourea, acetamide, acetanilide, stearylamide, phthalic anhydride, metal stearates, dimethyl terephthalate, phthalonitrile or other appropriate fusible products which induce the simultaneous melting of the colour former and the developer. Thermographic recording materials preferably contain waxes, e.g. carnauba wax, montan wax, paraffin wax, polyethylene wax, condensates of higher fatty acid amides and formaldehyde, or condensates of higher fatty acids and ethylenediamine.

A further utility of the compounds of formulae (1) to (5) is the formation of a coloured image by means of the photocurable microcapsules described e.g. in German Offenlegungsschrift No. 3 247 488.

The invention is illustrated by the following Examples, in which percentages are by weight, unless otherwise indicated.

EXAMPLE 1

29.3 g of the quinazolone of formula

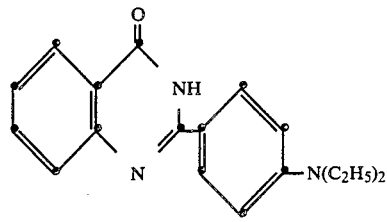

are reacted with 16 g of phosphoroxy chloride at 85°–90° C. in 70 g of toluene. The reaction mixture is stirred for 1 hour at this temperature to form a dark red solution of the 4-chloro-2-(4'-diethylaminophenyl)-quinazoline of formula

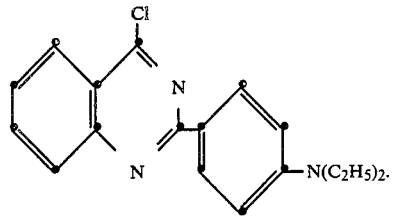

The solution is added dropwise to a suspension of 13.8 g of 2-phenoxyethanol, 10 g of a 50% solution of sodium hydroxide and 2 g of tetrabutylammonium bromide. The suspension is then stirred for 1½ hours at 100°–108° C. and subsequently extracted with 100 ml of water at 90° C. The toluene phase is separated and washed repeatedly with hot water. The toluene is removed by distillation and the residue is stirred into 320 g of methanol. The crystalline precipitate so formed is isolated by filtration at 15°–20° C., washed with methanol and water and dried, affording 24 g of a quinazoline of formula

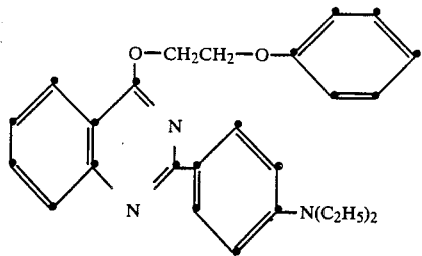

(21)

with a melting point of 116°–119° C. This readily soluble and sublimation-fast colour former develops on acid clay a strong greenish yellow colour of good lightfastness.

Following the procedure described in this Example, the quinazolines listed in the table are obtained using the appropriate starting materials.

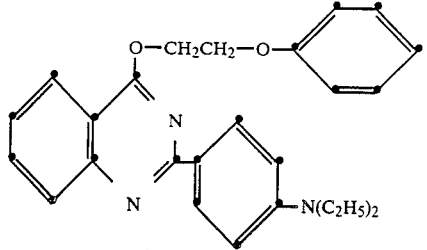

(21)

with a melting point of 116°–119° C. This readily soluble and sublimation-fast colour former develops on acid clay a strong greenish yellow colour of good lightfastness.

Following the procedure described in this Example, the quinazolines listed in the table are obtained using the appropriate starting materials.

TABLE $$Z_4-Q_3-Z_5-R_3$$
(structure with benzene fused to C=N-N=C-Y')

| Example | $Z_4$ | $Q_3$ | $Z_5$ | $R_3$ | Y' | m.p. in °C. | Colour |
|---|---|---|---|---|---|---|---|
| 2 | O | —CH$_2$CH$_2$CH$_2$— | O | phenyl | 4-N(C$_2$H$_5$)$_2$-phenyl | 107–108 | yellow |
| 3 | O | —CH$_2$CH$_2$— | —N(C$_2$H$_5$)— | phenyl | 4-N(C$_2$H$_5$)$_2$-phenyl | 90–92 | yellow |
| 4 | O | —CH$_2$CH$_2$— | morpholino | | 4-N(C$_2$H$_5$)$_2$-phenyl | 84–86 | yellow |
| 5 | O | —CH$_2$CH$_2$— | O | phenyl | 4-[N(C$_2$H$_5$)(CH$_2$CH$_2$-phenyl)]-phenyl | 114–116 | yellow |
| 6 | O | —CH$_2$CH$_2$— | O | phenyl | 4-[N(CH$_3$)(phenyl)]-phenyl | 140–142 | yellow |
| 7 | O | —CH$_2$CH$_2$— | O | phenyl | 4-N(CH$_2$-phenyl)$_2$-phenyl | 104–108 | yellow |

(22)

TABLE-continued $$Z_4-C(=N)-Q_3-Z_5-R_3 \quad ; \quad C(-Y')=N \quad (22)$$

| Example | $Z_4$ | $Q_3$ | $Z_5$ | $R_3$ | $Y'$ | m.p. in °C. | Colour |
|---------|-------|-------|-------|-------|------|-------------|--------|
| 8 | S | —CH₂CH₂— | O | phenyl | 4-N(C₂H₅)₂-phenyl | 90–91 | orange |
| 9 | O | —CH₂CH₂— | O | 4-Cl-phenyl | 4-N(C₂H₅)₂-phenyl | 109–110 | yellow |
| 10 | O | —CH₂CH₂— | O | 4-CH₃-phenyl | 4-N(C₂H₅)₂-phenyl | 104–105 | yellow |
| 11 | O | —CH₂CH₂— | O | 4-OCH₃-phenyl | 4-N(C₂H₅)₂-phenyl | 109–111 | yellow |
| 12 | O | —CH₂CH₂— | O | phenyl | 4-N(C₂H₄—CN)(CH₃)-phenyl | 163–164 | yellow |

TABLE-continued (22)

$$Z_4-Q_3-Z_5-R_3$$
with C=N, N=C-Y' ring structure

| Example | $Z_4$ | $Q_3$ | $Z_5$ | $R_3$ | $Y'$ | m.p. in °C. | Colour |
|---------|-------|-------|-------|-------|------|-------------|--------|
| 13 | O | —CH$_2$CH$_2$— | O | naphthyl | C$_6$H$_4$—N(C$_2$H$_5$)$_2$ | 146–148 | yellow |
| 14 | O | —CH$_2$CH$_2$— | O | phenyl | C$_6$H$_4$—N(CH$_3$)$_2$ | 154–157 | yellow |
| 15 | O | —CH$_2$CH$_2$— | O | phenyl | C$_6$H$_3$(OCH(CH$_3$)$_2$)—N(C$_2$H$_5$) | 111–113 | yellow |

EXAMPLE 16

Preparation of a pressure-sensitive copying paper

A solution of 3 g of the quinazoline of formula (21) in 80 g of partially hydrogenated terphenyl and 17 g of kerosene are microencapsulated by coacervation in a manner known per se with gelatin and gum arabic. The microcapsules are mixed with starch solution and coated on a sheet of paper. The face of a second sheet of paper is coated with acid-activated bentonite as colour developer. The first sheet and the sheet coated with the developer are laid on top of each other with the coated sides face to face. Pressure is exerted on the first sheet by writing by hand or type-writing and a strong yellow copy of excellent fastness to light develops immediately on the sheet coated with the developer.

Comparably strong, lightfast yellow copies are obtained by using any of the other colour formers of formula (22) in Examples 2 to 15.

EXAMPLE 17

The procedure as described in Example 16 is repeated, replacing the quinazoline of formula (21) by a mixture of the following composition:
1.4 g of 3,3-bis(4'-dimethylaminophenyl)-6-dimethylaminophthalide,
1.0 g of N-butylcarbazol-3-yl-bis(4'-N-methyl-N-phenylaminophenyl)methane,
0.6 g of the quinazoline of formula (21) and
0.5 g of 3,3-bis(N-n-octyl-2'-methylindol-3'-yl)phthalide.

A pressure-sensitive recording material which gives a strong and lightfast black copy by writing by hand or typewriter is obtained.

EXAMPLE 18

1 g of the quinazoline of formula (21) is dissolved in 17 g of toluene. With stirring, 12 g of polyvinyl acetate, 8 g of calcium carbonate and 2 g of titanium dioxide are added to this solution. The resultant suspension is diluted with toluene in the weight ratio 1:1 and applied to a sheet of paper with a knife to a thickness of 10 μm. On this sheet of paper is laid a second sheet, the underside of which has been coated to a weight of 3 g/m² with a mixture consisting of 1 part of an amide wax, 1 part of a stearin wax and 1 part of zinc chloride. Pressure is exerted on the top sheet by hand or typewriter and a strong, lightfast yellow copy develops immediately on the sheet coated with the colour former.

EXAMPLE 19

Preparation of a heat-sensitive recording material

In a ball mill, 32 g of 4,4'-isopropylidenediphenol (bisphenol A), 3.8 g of the distearylamide of ethylenediamine, 39 g of kaolin, 20 g of an 88% hydrolysed polyvinyl alcohol and 500 ml of water are ground to particle size of about 5 μm. In a second ball mill, 6 g of the compound of formula (21), 3 g of a 88% hydrolysed polyvinyl alcohol and 60 ml of water are ground to a particle size of about 3 μm.

Both dispersions are mixed and applied to paper to a dry coating weight of 5.5 g/m². A strong yellow colour of excellent lightfastness is produced by contacting the paper with a heated ball-point pen.

Strong lightfast yellow colours can also be obtained by using any of the other colour formers of formula (22) indicated in Examples 2 to 15.

What is claimed is:
1. A chromogenic quinazoline of the formula

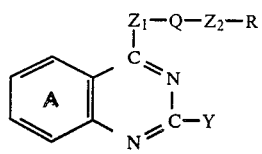

wherein
R is a phenyl, biphenylyl or naphthyl radical, each unsubstituted or substituted by halogen, cyano, nitro, lower alkyl, lower alkoxy, lower alkoxycarbonyl or lower alkylcarbonyl, or R is an aromatic heterocyclic radical selected from the group consisting of thienyl, furyl, pyrrolyl, pyrazolyl, imidazolyl and pyridyl, each unsubstituted or substituted by halogen, cyano, lower alkyl, lower alkoxy, lower alkoxycarbonyl or fused benzene, or R is a saturated heterocyclic radical selected from the group consisting of pyrrolidino, piperidino, pipecolino, morpholino, thiomorpholino, piperazino and N-methylpiperazino;
$Z_1$ is oxygen or sulfur;
$Z_2$ is oxygen, sulfur or —NR';
R' is hydrogen, alkyl of not more than 12 carbon atoms, unsubstituted or substituted by halogen, cyano or lower alkoxy, or is $C_5$–$C_6$cycloalkyl, phenyl, benzyl, phenethyl or $C_1$–$C_{12}$-acyl, or —NRR' is a 5- or 6-membered heterocyclic radical selected from the group consisting of pyrrolidino, piperidino, pipecolino, piperazino or morpholino;
Q is an aliphatic radical or an aliphatic radical which is interrupted by a further member $Z_2$;
Y is the radical of a couplable compound bound to the quinazoline moiety through a phenyl ring and is selected from the group consisting of unsubstituted, N-monosubstituted, or N,N-disubstituted aniline or naphthylamine, N-unsubstituted or N-substituted indole, indoline, carbazole, tetrahydrocarbazole, oxazine, thiazine, dihydroquinoline, tetrahydroquinoline, dibenzylimide or benzomorpholine wherein C-substituents are selected from the group consisting of halogen, hydroxyl, cyano, nitro, lower alkyl, lower alkoxy, lower alkoxycarbonyl, acyl of 1 to 8 carbon atoms, $C_1$–$C_4$acylamino, alkylene of 3 to 6 carbon atoms, cycloalkyl of 5 or 6 carbon atoms, benzyl and phenyl, and wherein N-substituents are selected from the group consisting of alkyl with 1 to 12 carbon atoms, alkenyl of 2 to 12 carbon atoms, cycloalkyl of 5 or 6 carbon atoms, phenyl, benzyl and phenethyl, each of which is unsubstituted or substituted by cyano, halogen, nitro, hydroxy, lower alkyl, lower alkoxy or lower alkoxycarbonyl, or when N is disubstituted the 2N-substituents and the nitrogen atom to which they are attached are a 5- or 6-membered heterocylic radical selected from the group consisting of pyrrolidino, piperidino, pipecolino, morpholino, thiomorpholino or piperazino; and the ring
A is unsubstituted or substituted by halogen, phenyl, cyano, nitro, lower alkyl, lower alkoxy or lower alkoxycarbonyl.

2. A quinazoline according to claim 1, wherein R is phenyl, biphenylyl or naphthyl, each unsubstituted or substituted by halogen, cyano, nitro, lower alkyl, lower alkoxy, lower alkoxycarbonyl or lower alkylcarbonyl.

3. A quinazoline according to claim 1, wherein R is phenyl, chlorophenyl, methoxyphenyl, tolyl or xylyl.

4. A quinazoline according to claim 1, wherein Q is $C_2$–$C_4$alkylene.

5. A quinazoline according to claim 1, wherein $Z_1$ and $Z_2$ are each oxygen.

6. A quinazoline according to claim 1, wherein Y is the radical of an N-monosubstituted or N,N-disubstituted aniline or naphthylamine.

7. A quinazoline according to claim 1, wherein Y is the radical of an N,N-disubstituted aniline.

8. A quinazoline according to claim 1, wherein Y is an indolinyl, tetrahydroquinolinyl or benzomorpholino radical.

9. A quinazoline according to claim 1, of formula

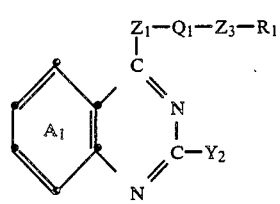

(3)

wherein $R_1$ is a phenyl or naphthyl radical, each unsubstituted or substituted by halogen, methyl or methoxy, $Z_1$ is oxygen or sulfur, $Z_3$ is oxygen, sulfur,

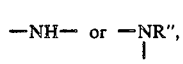

$R''$ is lower alkyl or —$NR_1R''$ is morpholino, $Q_1$ is $C_2$–$C_4$alkylene or the radical —(CH$_2$—CH$_2$—O)$_m$—CH$_2$CH$_2$—, $Y_2$ is an aminophenol radical of formula

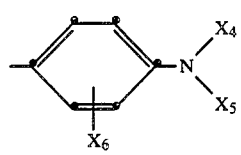

(3a)

or a 5-indolinyl radical of formula

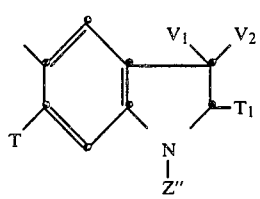

(3b)

or a tetrahydroquinolinyl radical of formula

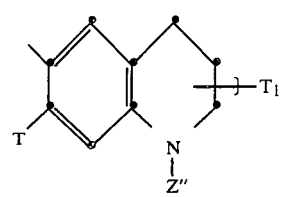

(3c)

or a tetrahydroquinolinyl radical of formula

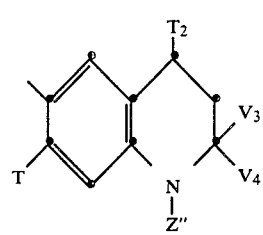

(3d)

or a benzomorpholino radical of formula

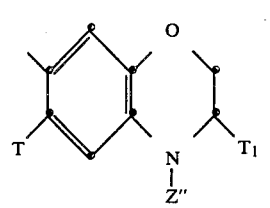

(3e)

wherein $m_1$ is 1 to 3, $X_4$ and $X_5$ are each independently of the other lower alkyl, cyano-lower alkyl, benzyl, phenyl, phenethyl, lower alkylphenyl or lower alkoxyphenyl; or $X_4$ and $X_5$, together with the nitrogen atom to which they are attached, are pyrrolidino, piperidino or morpholino, $X_6$ is hydrogen, halogen, lower alkyl or lower alkoxy, $Z''$ is hydrogen, $C_1$–$C_8$alkyl, $C_2$–$C_6$alkoxyalkyl, β-cyanoethyl, benzyl or phenethyl, T is hydrogen, halogen, lower alkyl, lower alkoxy, $C_1$–$C_4$acylamino or phenyl, $T_1$ and $T_2$ are each hydrogen, halogen, hydroxy, lower alkyl or lower alkoxy, and $V_1$, $V_2$, $V_3$ and $V_4$ are each hydrogen, lower alkyl, $C_5$–$C_6$cycloalkyl or benzyl; or ($V_1$ and $V_2$) or ($V_3$ and $V_4$) are each together $C_4$–$C_5$-alkylene, and the ring $A_1$ is unsubstituted or substituted by one or two members selected from cyano, halogen, lower alkyl, phenyl and lower alkoxy.

10. A quinazoline according to claim 9, wherein $Y_2$ is an aminophenyl radical of formula (3a).

11. A quinazoline according to claim 10, wherein $X_4$ and $X_5$ are each lower alkyl or benzyl, $X_6$ is hydrogen, $R_1$ is phenyl or chlorophenyl, $Q_1$ is ethylene or propylene, $Z_1$ and $Z_2$ are oxygen, and the ring $A_1$ is unsubstituted.

12. A quinazoline according to claim 1, of formula

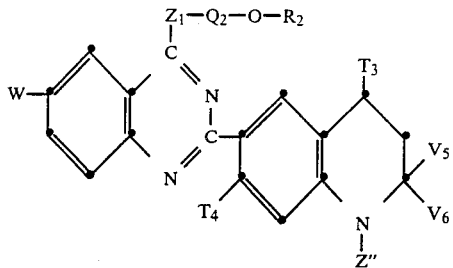

(4)

wherein

Q$_2$ is straight chain or branched C$_2$–C$_4$alkylene,

R$_2$ is phenyl, chlorophenyl, tolyl, methoxyphenyl or naphthyl,

Z$_1$ is oxygen or sulfur,

Z″ is C$_1$–C$_8$alkyl, β-cyanoethyl or benzyl,

T$_3$, V$_5$ and V$_6$ are each lower alkyl,

T$_4$ is hydrogen or methyl, and

W is hydrogen, halogen, methyl or methoxy.

13. A quinazoline according to claim 1, of formula

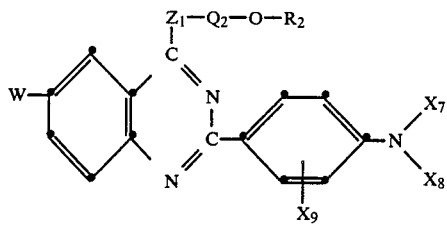

(5)

wherein

Q$_2$ is straight chain or branched C$_2$–C$_4$alkylene,

R$_2$ is phenyl, chlorophenyl, tolyl, methoxyphenyl or naphthyl,

Z$_1$ is oxygen or sulfur,

X$_7$ and X$_8$ are each lower alkyl or benzyl, or —NX$_7$X$_8$ is piperidino,

X$_9$ is hydrogen, halogen, methyl or methoxy and W is hydrogen, halogen, methyl or methoxy.

14. A quinazoline according to claim 13, wherein Q$_2$ is ethylene or propylene, R$_2$ is phenyl or chlorophenyl, X$_7$ and X$_8$ are each lower alkyl, and X$_9$ and W are each hydrogen.

15. A quinazoline according to claim 1 wherein Y is selected from the group consisting of N-unsubstituted or N-substituted indoline, tetrahydrocarbazole, dihydroquinoline, tetrahydroquinoline, dibenzylimide and benzomorpholine, which radical is attached to the quinazoline moiety through a fused benzene ring of said heterocycle.

16. A quinazoline according to claim 1 wherein Y is of the formula

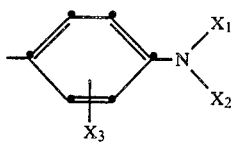

wherein

X$_1$ and X$_2$ are each independently of the other hydrogen, alkyl of 1 to 12 carbon atoms, unsubstituted or substituted by halogen, hydroxy, cyano or lower alkoxy, or are C$_5$–C$_6$cycloalkyl, phenyl, benzyl, phenethyl, or phenyl or benzyl, each substituted by halogen, nitro, cyano, lower alkyl, lower alkoxy or lower alkoxycarbonyl, or X$_1$ and X$_2$ together with the nitrogen atom to which they are attached are a 5- or 6-membered heterocyclic radical selected from the group consisting of pyrrolidino, piperidino, pipecolino, morpholino, thiomorpholino and piperazino, and X$_3$ is hydrogen, halogen, nitro, lower alkyl, lower alkoxy or lower alkoxycarbonyl.

* * * * *